United States Patent [19]
Hoover et al.

[11] Patent Number: 5,535,746
[45] Date of Patent: Jul. 16, 1996

[54] PREFILLED SYRINGE FOR USE WITH POWER INJECTOR

[75] Inventors: Linn C. Hoover, Webster; Raymond P. Chapman, Fairport; Daniel D. Adamson, Geneseo, all of N.Y.

[73] Assignee: Sterling Winthrop Inc., New York, N.Y.

[21] Appl. No.: 219,598

[22] Filed: Mar. 29, 1994

[51] Int. Cl.⁶ ........................................ A61B 6/00
[52] U.S. Cl. .................. 128/655; 604/152; 604/187; 604/131; 128/654
[58] Field of Search .................. 604/218, 228, 604/187, 232, 220–221, 152, 131; 128/654, 655

[56] References Cited

U.S. PATENT DOCUMENTS

| | | | |
|---|---|---|---|
| 3,738,539 | 6/1973 | Beich | 604/218 |
| 3,811,441 | 5/1974 | Sarnoff | 604/232 |
| 4,861,581 | 8/1989 | Epstein et al. | 424/1.1 |
| 5,019,371 | 5/1991 | Lin et al. | 424/5 |
| 5,254,101 | 10/1993 | Trombley, III | 604/232 |
| 5,300,031 | 4/1994 | Neer et al. | 604/218 |
| 5,318,767 | 6/1994 | Liversidge et al. | 424/4 |
| 5,383,858 | 1/1995 | Reilly et al. | 604/187 |

*Primary Examiner*—Krista M. Zele
*Assistant Examiner*—Brian L. Casler
*Attorney, Agent, or Firm*—Fish & Richardson

[57] ABSTRACT

A plastic syringe adapted for use with power injector systems comprises a cylindrical barrel for receiving a liquid, a plunger axially reciprocable within the barrel for discharging the liquid therefrom, a discharge extension at the distal end of the barrel terminating in a discharge outlet, at least one radially outwardly extending mounting lug located at or near the outer proximal end of the barrel, the lug having a distal surface having first and second ends defining a constrained portion of the barrel, and the lug being crown shaped such that the center of the distal surface of the lug is distally offset from the ends of the lug. In another embodiment, the syringe comprises a cylindrical collar adapted to fit over and attach to the proximal end of the cylindrical barrel, and the crowned lug is located at or near the outer proximal end of the collar. The crowned lug reduces stresses on the lug during injection, thus providing improved reliability and enabling the syringe to be fabricated of lower modulus autoclavable plastics.

12 Claims, 5 Drawing Sheets

PREFILLED SYRINGE FOR USE WITH POWER INJECTOR

BACKGROUND OF THE INVENTION

1. Field of Invention

This invention relates to a novel plastic syringe. More specifically, this invention relates to a plastic syringe for use with a power injector.

2. Description of the Related Art

The use of contrast media for image enhancement in medical diagnostic imaging is widespread. For example, x-ray contrast agents, which are typically iodinated contrast agents, such as the nonionic contrast agent iohexol, have gained widespread commercial acceptance in various x-ray imaging procedures such as x-ray computed tomography (CT).

To effect introduction of contrast media into body cavities such as the vascular network, it has been common practice to utilize injector syringes in combination with catheters. The syringe can be mounted in a power injector apparatus, with the distal end of the syringe being connected to the catheter which is introduced into the system to be studied. It has been estimated recently that of the approximately 9 million contrast enhanced CT scans performed in the United States each year, about one-half involve power injectors and the number is growing. Additionally, approximately 90% of the 1.3 million cardiac angiographic procedures which take place annually in the United States involve power injectors.

The use of prefilled syringes, i.e., syringes prefilled with a unit dose, e.g., of contrast media, with such power injectors provides greater convenience and safety to the health care worker while minimizing waste. For example, the need to transfer contrast media from glass containers to empty syringes can be entirely eliminated. Additionally, risks of contamination associated with preparing sterile contrast agent for injection into the patient can be reduced.

Power injectors for various CT procedures such as angiography are described, e.g., in U.S. Pat. No. 4,006,736; U.S. Pat. No. 4,677,980; U.S. Pat. No. 4,854,324; U.S. Pat. No. 4,911,695; and U.S. Pat. No. 5,007,904. The power injectors described in these patents are of the rear-loading type, i.e., syringes are rear-loaded into a pressure jacket of the injector. More specifically, these injectors comprise a rotatable turret which carries a pair of the pressure jackets and which is rotatable so that when one of the pressure jackets into which a syringe has been rear-loaded is in an injection position, the other pressure jacket is in a position in which a syringe can be rear-loaded. Subsequently, when injection of liquid from the first syringe is completed, the turret is rotated to move the first syringe to an unloading position. When the pressure jacket and its associated syringe has been located in the injection position, a drive member of the injector is moved forward to become drivingly engaged with a plunger in the syringe.

European Patent Application No. 584,531 describes a front-loading medical injector wherein a syringe is mountable upon and removable from a front wall of an injector housing or mounting plate. The front-loading injector includes a readily releasable mechanism for supporting the syringe on the front wall of an injector housing for an injection operation. The releasable mechanism includes at least one retaining portion on the mounting mechanism releasably engageable with a mating retaining portion on the syringe. In addition to enhanced setup convenience, such a front-loading injector provides additional advantages to the health care worker. By not being enclosed in a pressure jacket, the health care worker is better able to view the status of the syringe visually during an injection operation. By allowing the health care worker to better see the syringe, the worker can readily determine whether the syringe is empty or full, the amount of contrast medium delivered, the presence or absence of bubbles, etc.

Heretofore, plastic syringes have been provided for such front-loading power injectors. One such syringe comprises a set of radially extending lugs spaced 180 degrees apart which engage two mating slots in a mounting plate on the power injector by inserting the syringe lugs into the slots and rotating the syringe 90 degrees. This design has achieved some success with a syringe fabricated of polyethylene terephthalate (PET). However, this and other designs proposed in European Patent Application No. 584,531 are less than adequate for some plastics, particularly those of low modulus and/or yield strength, due to the fact that stresses generated during injection can cause localized and/or complete shearing of the lug off the barrel.

Furthermore, PET, when autoclaved at 210° F., undergoes a phase transition from a clear amorphous state to an opaque crystalline state. This is undesirable because one of the dangers associated with the injection of fluids into a patient is a the risk that air will be accidentally injected into the patient. The presence of a transparent syringe barrel enables the health care worker to readily detect empty and/or partially filled syringes prior to an attempted injection. Thus, it would be highly desirable to be able to replace PET in a plastic syringe for use with power injectors with other plastic materials which can be autoclaved without compromising clarity.

SUMMARY OF THE INVENTION

We have discovered that localized stresses generated in the lug of a prefilled plastic syringe during injection with a power injector can be unexpectedly reduced and more evenly distributed by crowning the distal surface of the lug. Surprisingly, stress reduction of over 50% can be achieved. This enables prefilled syringes for use in front-loading power injectors to be fabricated of various plastics, including lower strength plastics such as a methylpentane copolymer and polypropylene, which have good clarity even after autoclaving.

More specifically, in accordance with this invention there is provided a plastic syringe comprising a cylindrical barrel for receiving a liquid, a plunger axially reciprocable within the barrel for discharging the liquid therefrom, a discharge extension at the distal end of the barrel terminating in a discharge outlet, at least one radially outwardly extending mounting lug located at or near the outer proximal end of the barrel, the lug having a distal surface having first and second ends defining a constrained portion of the barrel, and the lug being crown shaped such that the center of the distal surface of the lug is distally offset from the ends of the lug. In a preferred embodiment, the syringe comprises two mounting lugs spaced 180 degrees apart with respect to the barrel.

In another aspect, this invention provides a plastic syringe featuring a barrel, plunger and discharge extension as described above, a cylindrical collar adapted to fit over and attach to the proximal end of the barrel, and at least one mounting lug as described above located at or near the outer proximal end of the collar.

In another embodiment, this invention provides a power injector system comprising a mounting plate adapted to receive a syringe, a driving mechanism including head and shaft elements, and a plastic syringe as described above mounted on the plate, wherein the plunger of the syringe selectively engages with the head and shaft elements of the driving mechanism.

It is an advantageous feature of this invention that a syringe is provided which can be fabricated of low strength, autoclavable plastics such as a methylpentene copolymer or polypropylene and used in conjuction with commercially available power injectors.

It is another advantageous feature of this invention that an autoclavable plastic syringe is provided which can be prefilled with the contrast media iohexol and used in conjunction with commercially available power injectors.

Another advantageous feature of this invention is that a plastic syringe is provided for use with a power injector which more uniformly distributes injection pressure across the lug face, thus improving the load bearing efficiency of the mounting lugs and providing improved overall reliability.

These and other advantages will become readily apparent upon reference to the following description of the preferred embodiments when read in light of the accompanying drawings.

DETAILED DESCRIPTION OF PREFERRED EMBODIMENTS

This invention is hereinafter described in reference to preferred embodiments featuring a prefilled autoclavable plastic syringe for use with a front-loading power injector. However, the invention is believed to be applicable to any syringe designed for high injection pressures and featuring mounting lugs with unconstrained barrel sections between the lugs.

Figure 1:
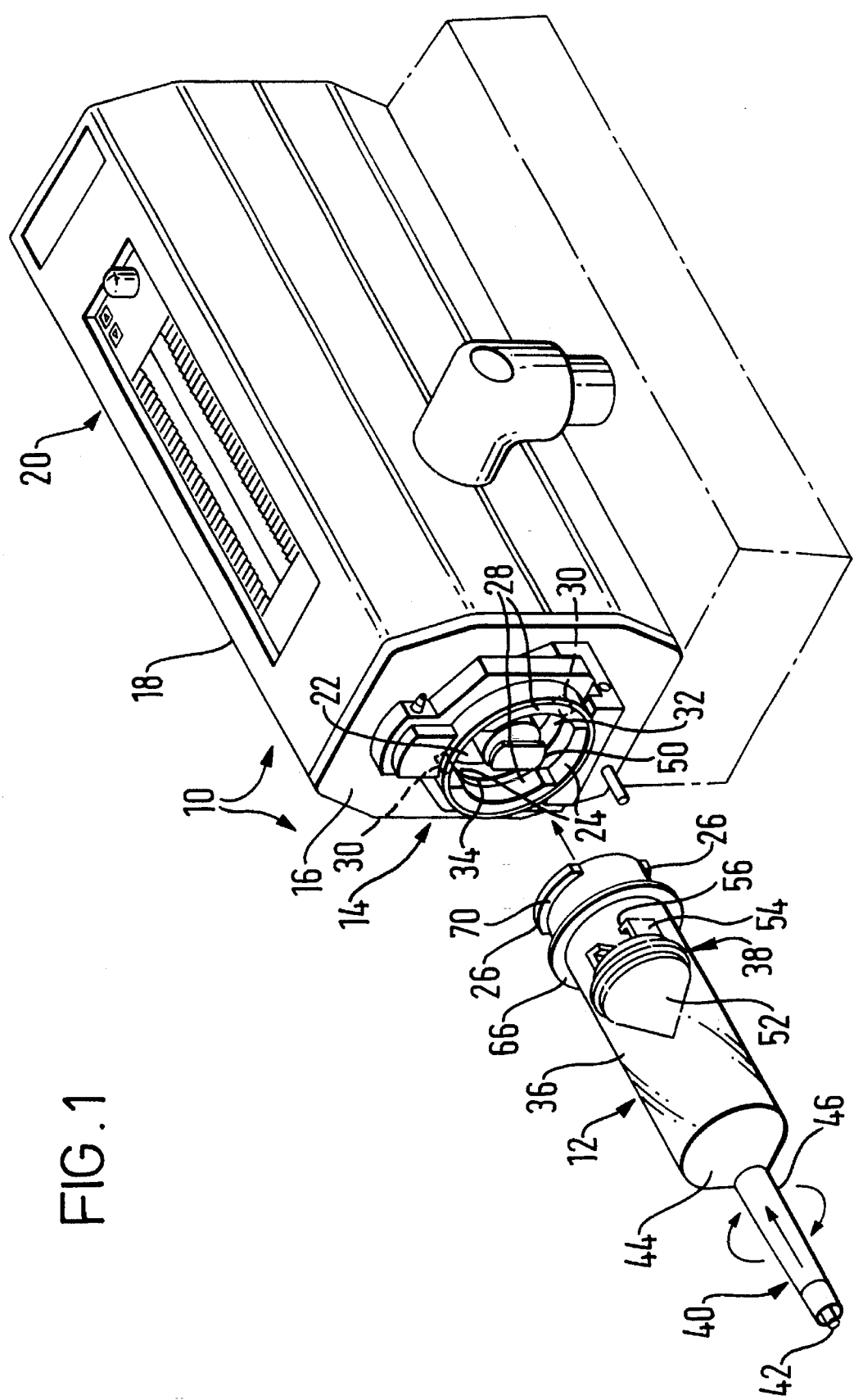
FIG. 1 is a partial isometric view of a plastic syringe and power injector of this invention showing an injector housing featuring a mounting plate and a syringe in disassembled relationship.

The syringe of this invention is particularly useful in conjunction with a front-loading power injector such as is depicted in FIG. 1. Front-loading injector apparatus 10 utilizes syringe 12 capable of being front-loaded onto mounting plate 14 on front wall 16 of housing 18 of injector 20. The mounting plate on the front wall of the housing is provided with an essentially cylindrical opening 22 for receiving the proximal end of the syringe. The opening includes at least one, and more preferably, a pair of upper and lower slots 24 through which mounting lugs 26 of the syringe may pass as the proximal end of the syringe is inserted into the opening. The mounting assembly further includes opposed retaining flanges 28 on opposite sides thereof so that after the proximal end of the syringe has been inserted into the opening, and the syringe is rotated clockwise, the mounting lugs on the syringe become engaged behind the retaining flanges to secure the syringe to the housing front wall. During mounting, the rotation of the syringe can be limited by suitable rearwardly projecting stops 30 at adjacent ends of the retaining flanges in the mounting plate. The mounting plate can also include inner annular ring 32 in spaced relationship to the retaining flanges to provide support for the proximal end of the syringe and define semi-annular guide slots 34 for receiving the mounting lugs.

Figure 2:
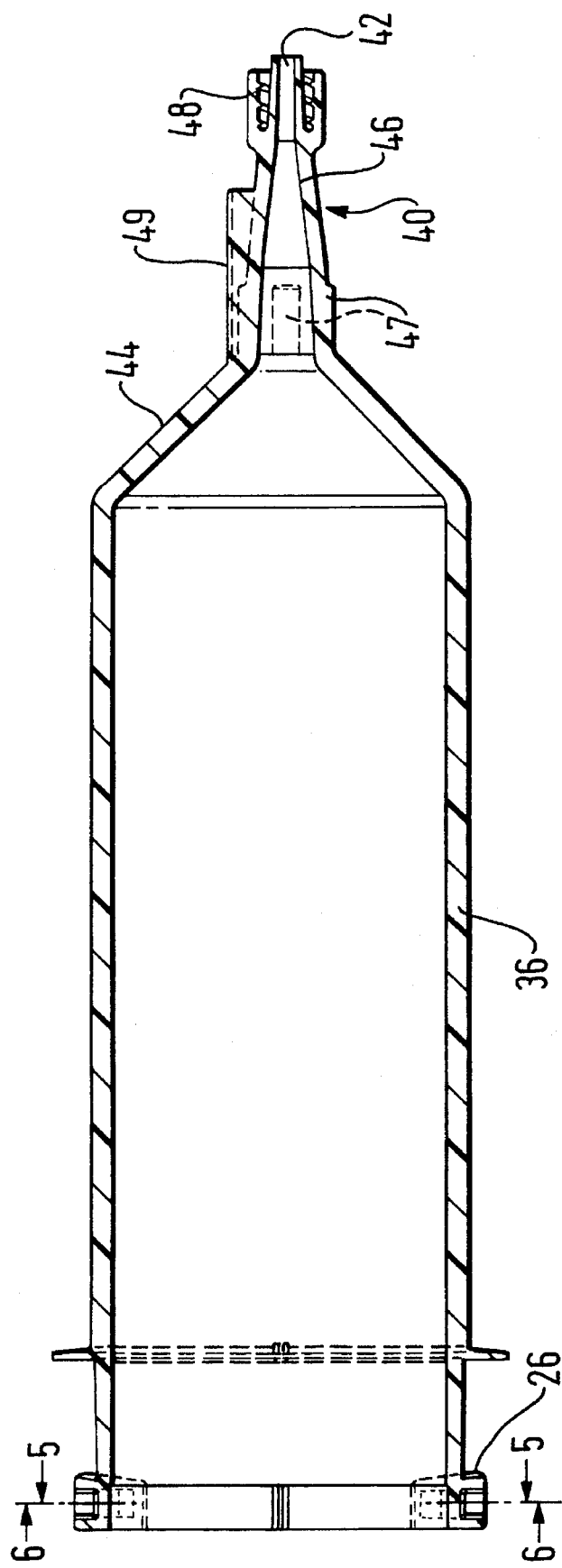
FIG. 2 is a cross-sectional view of a preferred embodiment of a plastic syringe according to this invention, without an associated plunger.

The syringe of this invention comprises a generally cylindrical barrel 36 enclosing an interior volume for receiving a liquid. Plunger 38 is axially reciprocable within the barrel and is slidably mounted, in engagement, with the inner wall surface of the cylindrical barrel. At its distal end, the barrel has discharge extension 40 terminating in tubular discharge outlet 42. In preferred embodiments, the barrel is joined via frustoconical section 44 to distal tapered section 46 which in turn is joined to the tubular discharge outlet. The tapered section of the syringe optionally features, on a portion of its exterior surface, thread 48 (FIG. 2) which can be employed for coupling the syringe, via a complementary threaded connected fitting, to a catheter or the like (not shown). The syringe can be provided with one or more guide extensions 47 and/or alignment edge 49 to facilitate assemblage of the syringe with various power injector designs.

Figure 3:
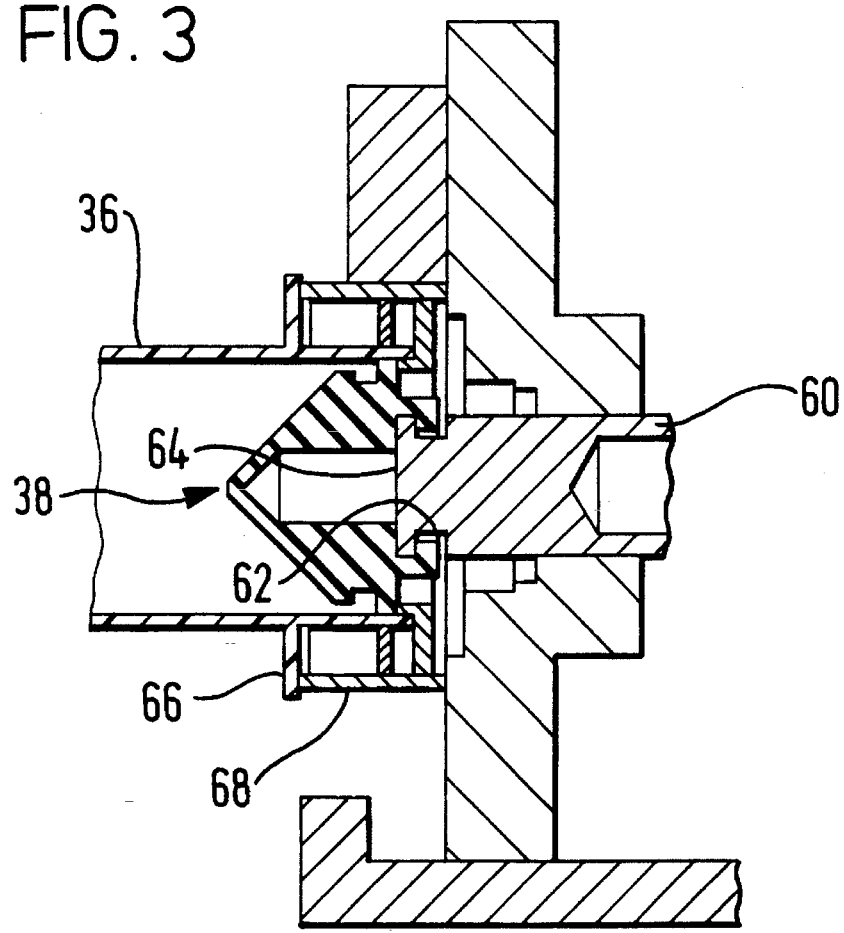
FIG. 3 is a partial cross-sectional view illustrating an injector housing featuring a mounting plate and a syringe in assembled relationship.

The plunger is slidably positioned within the cylindrical barrel for discharging the liquid from the barrel through the discharge outlet. The plunger can be connectable to driving member 50 in the injector housing, preferably by a readily releasable mechanism formed in part by the plunger comprising base member 52 having hook members 54 or the like extending rearwardly therefrom. Portions 56 of these members extend radially inward in opposed relationship. The hook members are designed to facilitate axial movement of the plunger in either direction when connected to the driving member by the releasable mechanism. An actuating mechanism can cause the drive member to reciprocate the plunger in the syringe body. The drive member comprises base portion 60 (FIG. 3), stem 62 and rectangular head 64 extending radially from the stem. The syringe can be provided with sealing ring 66 which engages outer annular ring 68 when the syringe is inserted into the opening in the mounting plate.

In a preferred embodiment, the plunger can comprise a body and a sheath such as is described in U.S. Pat. No. 5,007,904. The plunger body can be fabricated of any suitable material of construction which is advantageously employed in the use environments with which the syringe is associated. The plunger body may be formed of a generally stiff, resilient material such as a hard elastomer or alternatively it may be formed of any other suitable natural or synthetic, polymeric or nonpolymeric material. In practice, plastics are generally preferred. Preferred materials include polycarbonate and polyphenylene oxide, such as the polyphenylene oxide material commercially available from General Electric Company under the trademark Valox®. The sheath portion of the plunger, which slidably contacts the inner wall of the cylindrical barrel, can be formed of any suitable material which is advantageously employed in the environments with which the plunger is associated. Preferred materials of construction include rubber materials, with natural rubber being preferred.

Figure 4:
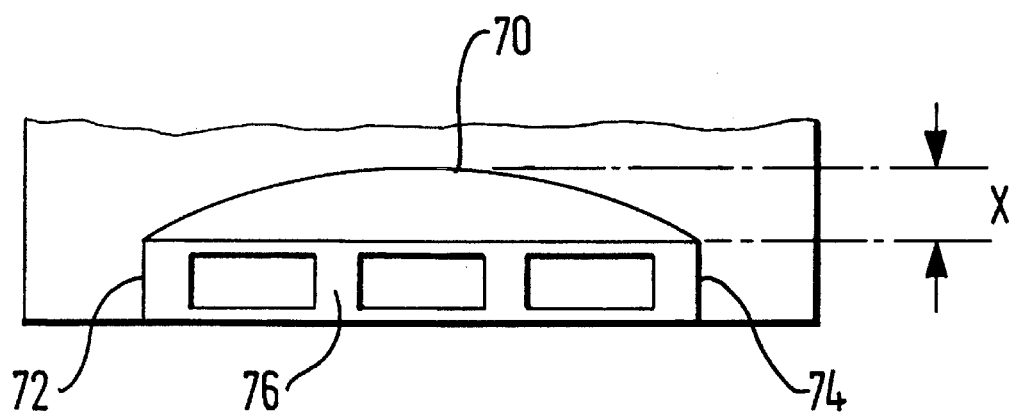
FIG. 4 is a partial top plan view of a syringe of this invention illustrating a crowned mounting lug featuring reinforcing ribs and having a crown thickness represented by X.
Figure 5:
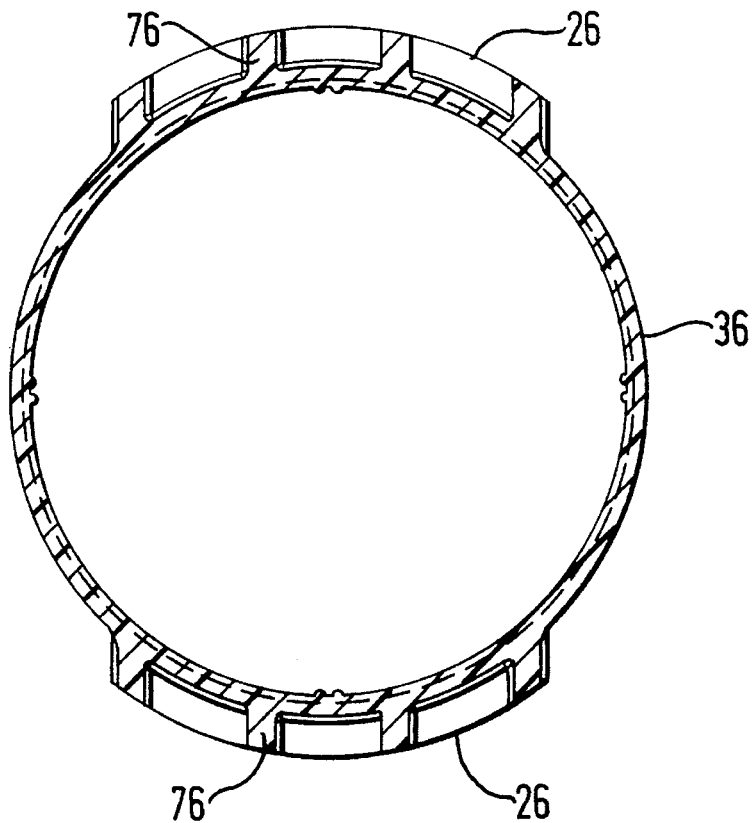
FIG. 5 is an end view, as seen along the line 5—5 in FIG. 2, illustrating an embodiment of a syringe of this invention having a pair of crowned mounting lugs featuring reinforcing ribs.
Figure 6:
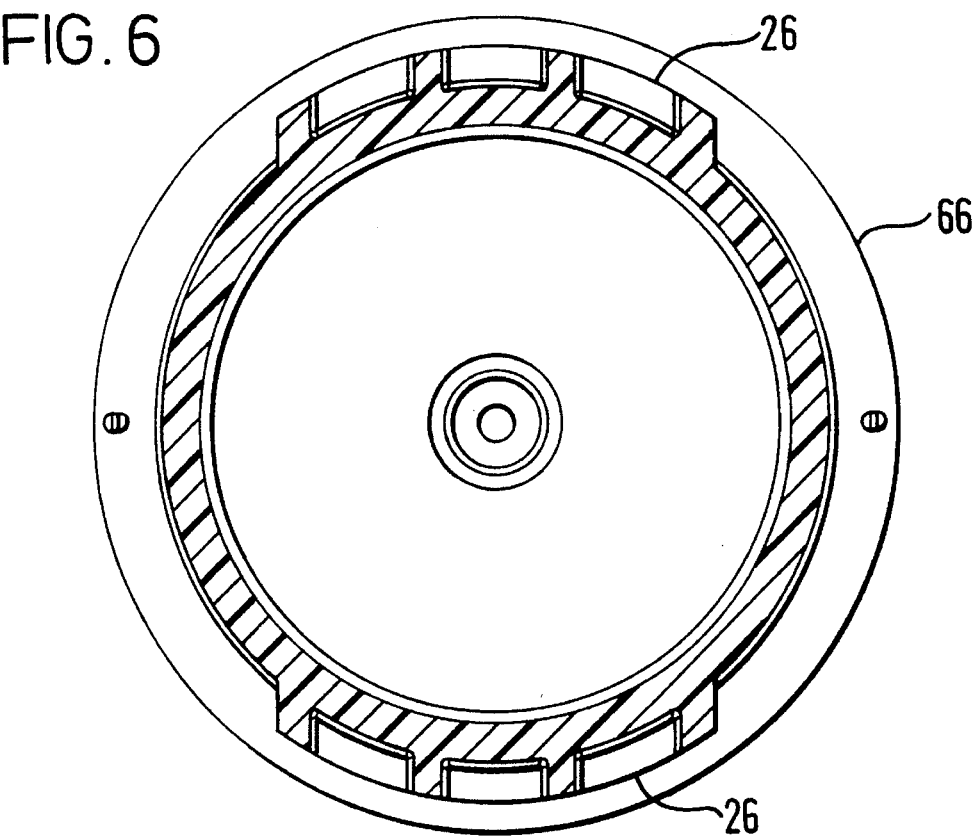
FIG. 6 is an end view, as seen along the line 6—6 in FIG. 2, also illustrating the pair of crowned mounting lugs.

The syringe of this invention includes at least one radially outwardly extending mounting lug 26 located at or near the outer proximal end of the barrel. The mounting lug has distal surface 70 (FIG. 4) having first end 72 and second end 74 which define a constrained portion of the barrel. The lugs can be provided with reinforcing ribs 76. The lug has a crown shape, i.e., the center of the distal surface of the lug is distally offset from the ends of the lug. The distal surface of the lug preferably is arcuately shaped. In a preferred embodiment, as illustrated best in FIGS. 5 and 6, the syringe comprises a pair of mounting lugs spaced 180 degrees apart with respect to the barrel.

The lug can comprise a generally solid crowned shoulder, as depicted in FIG. 1, a reinforced ribbed design, such as is depicted in FIGS. 2, 4, 5 and 6, or any other shape which provides the advantages described herein.

The preferred thickness X of the crown, i.e., the amount by which the center of the distal surface of the lug is distally offset from the ends of the lug (see FIG. 5), is determined primarily by the modulus and yield strength of the plastic, injection pressures and syringe wall thickness. In preferred embodiments, the crown thickness is at least about 0.025 cm (0.01 inch) and more preferably, at least about 0.060 (0.025 inch). For a syringe described above, a crown thickness of 0.075 cm (0.030 inch) is most preferred for injection pressures of 300–400 PSI (21.1–28.1 kg/cm$^2$). Higher pressures would require more crown while lower pressures would require less.

While Applicants do not wish to be bound by theoretical mechanisms, deflection plots from extensive finite element analyses suggest that unconstrained portions of the syringe, e.g., portions between the lugs, during injection are pulled forward by injection forces, causing the lugs to curl and forcing the front edges of the lugs into the mounting plate, thus concentrating stresses at the end points of the lugs. The crowned lug design of this invention permits the center of the lug to contact the mounting plate first during high pressure injections. The natural deflection of the syringe under such high injection pressures flattens the lug and distributes the forces over a larger surface area, thus reducing the overall stress in the lugs.

Figure 7:
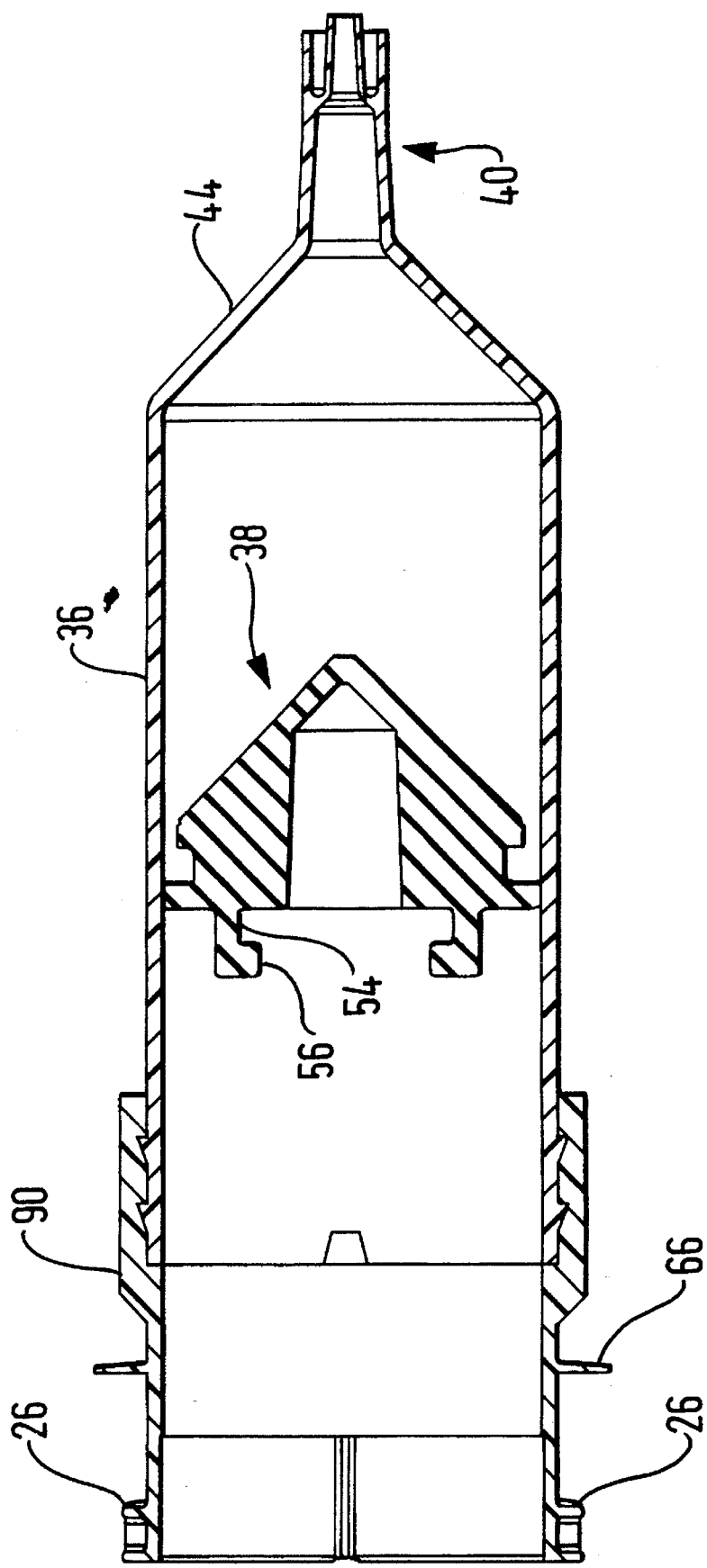
FIG. 7 is a cross-sectional view of an alternative embodiment of a syringe of this invention featuring a collar.

In another embodiment depicted in FIG. 7, the syringe includes cylindrical collar 90 adapted to fit over and attach to the proximal end of the cylindrical barrel. The collar can be attached to the barrel by conventional means, e.g., by a snap fit or by threading engagement. The collar has at least one radially outwardly extending mounting lug located at or near the outer proximal end of the collar. The lug has a distal surface having first and second ends defining a constrained portion of the collar. In preferred embodiments, the lug is crown shaped, such that the center of the distal surface of the lug is distally offset from the ends of the lug, as defined above. This "two-piece" design provides several advantages. First, the mating collar can be fabricated of a different, e.g., higher modulus, plastic than the barrel inasmuch as it can be assembled onto the barrel after the autoclave cycle. Second, any changes to the injector mounting plate which interfaces with the syringe could be accommodated by changing only the collar, and consequently would not necessarily affect that portion of the prefilled syringe subject to regulatory approval. In other words, any design changes to the exterior of a one-piece syringe could require recertification of the entire prefilled package. Third, this "two-piece" design featuring a collar can be easily and readily adapted to various power injectors merely by designing a separate collar for each type of injector/syringe mounting interface.

A power injector according to this injector comprises a mounting plate adapted to receive a syringe as described above, and a driving member including head and shaft elements. The head and shaft elements of the driving member can selectively engage the plunger of the syringe by any of a variety of conventional techniques well known in the art.

As noted, it is an advantageous feature that this invention enables prefilled syringes for use in front-loading power injectors to be fabricated of lower modulus plastics such as a methylpentene copolymer and polypropylene. However, the syringe according to this invention can be fabricated of any suitable plastic such as polycarbonate, polysulfone, polyethylene terephthalate, amorphous polyolefin, polypropylene, polyphenylene oxide, methylepentene copolymer and the like. A preferred plastic is a methylpentene copolymer available from Mitsui Petrochemical Industries, Ltd., New York, N.Y., under the tradename TPX RT18; having the structural formula

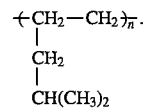

In any event, the use of this invention in conjunction with higher modulus plastics, such as PET, results in improved overall reliability and facilitates high injection forces. Additionally, the crowned lug design of this invention enables the lug to be fabricated of less material, thus saving material costs.

The syringe of this invention is useful in conjunction with any liquid. Preferred liquids include therapeutic and/or diagnostic agents. In particularly preferred embodiments, the liquid is a diagnostic imaging contrast media comprising a diagnostic imaging contrast agent. In the most preferred embodiments, the liquid is an x-ray contrast media featuring an x-ray contrast agent. A particularly preferred x-ray contrast agent is iohexol. Other contrast media for x-ray imaging which are in commercial or clinical use include iodixanol, metrizamide, iopamidol, ioversol, iotrolan, iopromide, ioxalan, hexabrix (ioxaglate meglumine and ioxaglate sodium), iothalamate meglumine, iothalamate sodium, diatrizoate meglumine and diatrizoate sodium. The invention is also useful in conjunction with plastic syringes filled with liquid contrast media for ultrasound imaging and magnetic resonance imaging procedures.

The invention has been described in detail with particular reference to certain preferred embodiments thereof, but it will be understood that variations and modifications can be effected within the spirit and scope of the invention.

We claim:

1. A plastic syringe comprising:

a cylindrical barrel for receiving a liquid, said barrel having a distal end and a proximal end;

a plunger axially reciprocable within said barrel for discharging the liquid therefrom;

a discharge extension at the distal end of said barrel terminating in a discharge outlet;

at least one radially outwardly extending mounting lug located at or near an outer portion of the proximal end of said barrel, said lug having a distal surface having first and second ends defining a constrained portion of said barrel, and said lug being crowned shaped such that the center of the distal surface of said lug is distally offset from the ends of the distal surface of said lug in a direction extending towards the distal end of said barrel.

2. The plastic syringe of claim 1 comprising two of said mounting lugs spaced 180 degrees apart with respect to said barrel.

3. The plastic syringe of claim 1 wherein the center of the distal surface of said lug is distally offset by at least 0.025 cm from the ends of said lug.

4. The plastic syringe of claim 1 wherein the center of the distal surface of said lug is distally offset by at least 0.06 cm from the ends of said lug.

5. The plastic syringe of claim 1 wherein said liquid comprises a diagnostic imaging contrast agent.

6. The plastic syringe of claim 5 wherein said diagnostic imaging contrast agent is an x-ray contrast agent.

7. The plastic syringe of claim 6 wherein said x-ray contrast agent is selected from the group consisting of iohexol, iodixanol, ioversol, metrizamide, iopamidol, iotrolan, iopromide, ioxalan, hexabrix, iothalamate meglumine, iothalamate sodium, diatrizoate meglumine and diatrizoate sodium.

8. The plastic syringe of claim 7 wherein said x-ray contrast agent is iohexol.

9. The plastic syringe of claim 1 wherein said syringe is formed from a plastic selected from the group consisting of polycarbonate, polysulfone, polyethylene terephthalate, amorphous polyolefin, polyphenylene oxide, polypropylene and methylpentene copolymer.

10. A power injector system comprising a plastic syringe according to claim 1, a mounting plate on which said plastic syringe is mounted, and a driving mechanism including head and shaft elements, wherein the plunger of said plastic syringe selectively engages with the head and shaft elements of said driving mechanism.

11. A plastic syringe comprising:

a cylindrical barrel for receiving a liquid, said barrel having a distal end and a proximal end;

a plunger axially reciprocable within said barrel for discharging liquid therefrom;

a discharge extension at the distal end of said barrel terminating in a discharge outlet;

a cylindrical collar having a distal end and a proximal end, said collar being adapted to fit over and attach to the proximal end of said cylindrical barrel;

at least one radially outwardly extending mounting lug located at or near an outer portion of the proximal end of said collar, said lug having a distal surface having first and second ends defining a constrained portion of said collar; and said lug being crown shaped such that the center of the distal surface of said lug is distally offset from the ends of the distal surface of said lug in a direction extending towards the distal end of said barrel.

12. A power injection system comprising a plastic syringe according to claim 11, a mounting plate on which said plastic syringe is mounted, and a driving mechanism including head and shaft elements, wherein the plunger of said syringe selectively engages the head and shaft elements of said driving mechanism.

* * * * *